United States Patent [19]
Dekeyser et al.

[11] Patent Number: 5,874,465
[45] Date of Patent: Feb. 23, 1999

[54] HYDRAZINECARBOXYLATE MITICIDES AND INSECTICIDES

[75] Inventors: Mark Achiel Dekeyser, Waterloo, Canada; Paul Thomas McDonald, Middlebury, Conn.

[73] Assignees: Uniroyal Chemical Company, Inc., Middlebury, Conn.; Uniroyal Chemical Co./CIE., Elmira, Canada

[21] Appl. No.: 736,309

[22] Filed: Oct. 24, 1996

[51] Int. Cl.⁶ .................... A01N 47/10; A01N 37/16; C07C 271/08
[52] U.S. Cl. .................... 514/482; 514/485; 514/484; 514/478; 514/539; 560/27
[58] Field of Search ................ 560/27; 514/485, 514/482, 484, 478, 539

[56] References Cited

U.S. PATENT DOCUMENTS

| | | | |
|---|---|---|---|
| 5,117,057 | 5/1992 | Hsu et al. | 564/149 |
| 5,225,443 | 7/1993 | Murphy et al. | 514/615 |
| 5,367,093 | 11/1994 | Dekeyser | 560/27 |
| 5,438,123 | 8/1995 | Dekeyser | 534/885 |
| 5,536,746 | 7/1996 | Dekeyser | 514/468 |
| 5,567,723 | 10/1996 | Dekeyser | 514/357 |

*Primary Examiner*—Shailendra Kumar
*Attorney, Agent, or Firm*—Daniel Reitenbach

[57] ABSTRACT

Compounds having the structural formula:

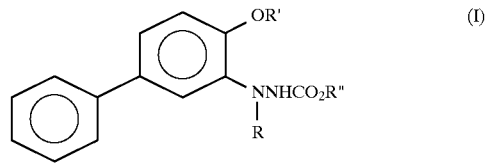

wherein:
R is $C_1$–$C_6$ hydroxyalkyl, $C_1$–$C_6$ haloalkyl, $C_1$–$C_6$ alkyl, $C_7$–$C_9$ aralkyl, or nitroso; R' is $C_1$–$C_4$ alkyl; and R" is $C_1$–$C_4$ alkyl. These compounds exhibit insecticidal and miticidal activity.

20 Claims, No Drawings

HYDRAZINECARBOXYLATE MITICIDES AND INSECTICIDES

FIELD OF THE INVENTION

This invention relates to novel hydrazinecarboxylate derivatives useful as insecticides and as miticides.

BACKGROUND OF THE INVENTION

Destruction of crops by insects and acarids presents a serious problem to agriculture. A wide variety of field crops are in need of protection from acarids and insects. Particularly difficult types of acarids and insects to control are those which, at one or more stages of their life, inhabit the soil and cause destruction to the roots of plants. Accordingly, the development of insecticides and miticides which are effective as ovicides, larvicides, and adulticides is desirable.

U.S. Pat. No. 5,438,123 describes certain phenylhydrazine derivatives useful as insecticides and acaricides.

SUMMARY OF THE INVENTION

This invention relates to a hydrazinecarboxylate derivative of the formula

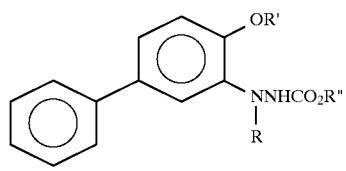
(I)

wherein:

R is $C_1$–$C_6$ hydroxyalkyl, $C_1$–$C_6$ haloalkyl, $C_1$–$C_6$ alkyl, $C_7$–$C_9$ aralkyl, or nitroso;

R' is $C_1$–$C_4$ alkyl; and

R" is $C_1$–$C_4$ alkyl.

The instant invention further relates to insecticidal compositions comprising:

a) an insecticidally effective amount of a compound of formula I; and (b) a suitable carrier.

The instant invention also relates to miticidal compositions comprising:

a) a miticidally effective amount of a compound of formula I; and (b) a suitable carrier.

The present invention is additionally directed to a method for controlling insects or mites which comprises applying an insecticidally or miticidally effective amount of a compound of formula I to the loci to be protected.

DETAILED DESCRIPTION OF THE INVENTION

Preferably, this invention relates to a a hydrazinecarboxylate derivative of the formula

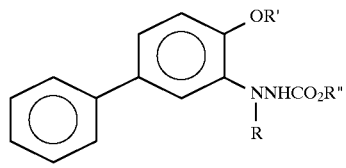
(I)

wherein:

R is $C_1$–$C_4$ hydroxyalkyl, $C_1$–$C_4$ haloalkyl, $C_1$–$C_4$ alkyl, $C_7$–$C_9$ aralkyl, or nitroso;

R' is methyl; and

R" is isopropyl.

More preferably, R is hydroxymethyl, 2-fluoroethyl, ethyl, propyl, benzyl, or nitroso;

R' is methyl; and

R" is isopropyl.

As used herein and in the claims, the term "alkyl", unless otherwise indicated, is meant to include both linear and branched alkyl.

The compounds of the instant invention can be prepared by reacting a hydrazinecarboxylate of formula A below with an alkylating agent, RX, wherein R is as described above (except nitroso and hydroxyalkyl) and X is bromine, chlorine, or iodine, and a base such as sodium or potassium carbonate, in a solvent such as acetonitrile or dimethylformamide.

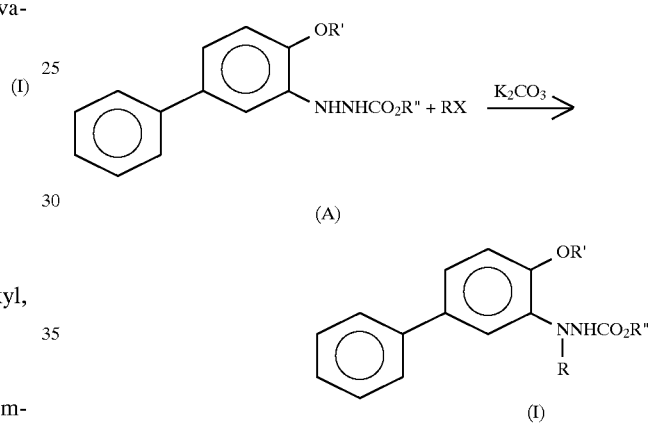

The compounds of formula I wherein R is nitroso, can be prepared by reacting a hydrazine carboxylate of formula A with sodium nitrite and hydrochloric acid in a solvent such as methanol or ethanol.

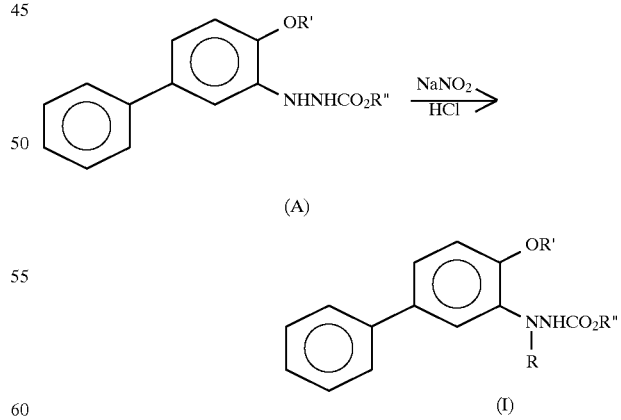

The compounds of formula I wherein R is $C_1$–$C_4$ hydroxyalkyl can be prepared by reacting a hydrazine carboxylate of formula A with an aldehyde, RO, wherein R is $C_1$–$C_4$ alkyl, in a solvent such as methanol or ethanol.

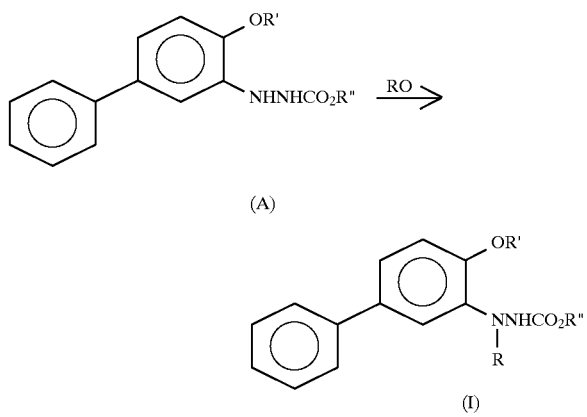

The insecticidal or miticidal compositions of this invention comprise (a) an insecticidally or miticidally effective amount of a compound of formula I; and (b) a suitable carrier. Suitable carriers useful in the composition of this invention can be agriculturally acceptable liquids, solids or mixtures thereof.

A liquid carrier useful in the composition of this invention, can be a solvent or a dispersant. In addition, two liquid carriers can be utilized, one serving as a solvent and the other as a dispersant.

In a preferred embodiment wherein the composition is a solution, the solvent carrier is usually an organic compound which can be polar or non-polar. Useful solvents include acetone, methanol, isopropanol, t-butyl alcohol, cyclohexanone, n-butyl alcohol, toluene, xylene, dioxane, dimethylformamide, dimethylsulfoxide, ethylene dichloride and N-methylpyrrolidone.

Another type of liquid composition within the contemplation of this invention is an emulsion. An emulsion is formed when the compound of formula I or formula II, is dispersed in water in the presence of a surface active agent. An emulsion is preferably formed by first preparing a solution of the type discussed in the above paragraph. The solution is then dispersed in water and a surface active agent is added thereto to form the emulsion. Surface active agents suitable for use in forming an emulsion useful in the composition of this invention, can be anionic, cationic or non-ionic, and are known in the art. *McCutcheon's Detergents and Emulsifiers*, Allured Publishing Corp., Ridgewood, N.J. (1970); U.S. Pat. No. 2,514,916 and U.S. Pat. No. 2,547,734, describe surface active agents useful in forming emulsions useful in the compositions of this invention.

A third type of liquid composition within the scope of this invention comprises a liquid dispersant as the carrier. In this embodiment, the compound of formula I, is dispersed in water in the absence of a surface active agent. Alternatively, the liquid composition comprises a solution of the compound of formula I, which, in turn, is dispersed in water, again in the absence of a surface active agent.

A fourth type of liquid composition within the scope of this invention, utilizes an aerosol. An aerosol is liquid under pressure but is gaseous at atmospheric pressure and ambient temperature. In most instances, an aerosol composition is prepared by first forming a solution of the compound of formula I in a conventional solvent of the type discussed above. This solution is then admixed with a volatile liquid aerosol under pressure in which condition the composition is applied.

Solid carriers useful in the composition of this invention include dusts, granules, wettable powders, pastes and water soluble solids. For example, compositions useful in this invention can be applied as a dust when the compound of formula I is adsorbed or absorbed onto or mixed with a powdered, solid carrier. A solid carrier such as a mineral silicate, e.g., mica, talc, pyrophyllite and clays, can be utilized for this purpose.

Additional solid compositions can be prepared from granular formulations of the compound of formula I and a granular or pelletized form of carrier such as granular clay, vermiculite, charcoal, corncobs, or the like. The use of granular formulations is particularly suitable for application by broadcasting, side-dressing, soil incorporation or seed treatment.

A mixture of a solid and liquid composition that employs both a liquid and a solid carrier, can also be used. Such a composition, for example, is prepared by dispersing a solid, on which the compound of formula I is absorbed or adsorbed, in a liquid dispersant. Such a composition preferably includes a surface active agent to maintain the solid particles dispersed in the liquid dispersant.

The composition of the present invention can utilize a carrier which is itself active. That is, the carrier can be a plant growth regulant, an insecticide, an acaricide, a fungicide, a bacteriacide, or the like.

It will be understood that the amount of the insecticidally or miticidally active compound in a given formulation will vary depending upon the specific pest to be combatted, as well as upon the specific chemical composition and formulation of the compound being employed, the method of applying the compound/formulation and the locus of treatment. Generally, however, concentrations of the compound as the active ingredient in insecticidally or miticidally effective formulations can range from about 0.1 to about 95 percent by weight. Spray dilutions can be as low as a few parts per million, while at the opposite extreme, full strength concentrates of the compound can be usefully applied by ultra low volume techniques. Concentration per unit area, where plants constitute the loci of treatment, can range between about 0.01 and about 50 pounds per acre, with concentrations of between about 0.1 and about 10 pounds per acre preferably being employed for crops such as corn, tobacco, rice and the like.

To combat insects and mites, sprays of the compounds can be applied to the insects or mites directly and/or to plants upon which they feed or nest. The compositions of this invention can also be applied to the soil or other medium in which the insects or mites are present.

Harmful insects and acarids attack a wide variety of plants, including both ornamental and agricultural plants and inflict damage by consuming roots and/or foliage, withdrawing vital juices from the plants, secreting toxins and often by transmitting diseases. The compounds of the present invention can be advantageously utilized to minimize or prevent such damage. The specific methods of application, as well as the selection and concentration of these compounds will vary depending upon such circumstances as geographic area, climate, topography, plant tolerance, etc. For specific circumstances, one skilled in the art can readily determine the proper compound, concentration and method of application by routine experimentation.

The compounds of the invention are particularly useful as insecticides and acaricides, for foliar and/or soil application. The compounds are particularly effective for controlling insects, such as corn rootworm, which live in the soil during one or more phases of their lives, by means of soil application.

EXAMPLES

The following examples are presented to illustrate the present invention.

Example 1

Preparation of 1-methylethyl 2-(4-methoxy-,[1,1'-biphenyl]-3-yl)-2-ethylhydrazinecarboxylate (Compound #1)

To 5 g of 1-methylethyl 2-(4-methoxy-[1,1'-biphenyl]-3-yl) hydrazinecarboxylate dissolved in 20 mL of dimethylformamide, was added 2.4 g of potassium carbonate and 4 g of iodoethane. The resulting mixture was refluxed with stirring overnight, then cooled to room temperature, diluted with 100 mL of water and extracted with diethyl ether (2×100 mL). After drying the diethyl ether portion over anhydrous sodium sulfate, the solvent was evaporated under reduced pressure. The resulting oil was purified by column chromatography, eluting with dichloromethane, to produce 3.2 g of an oil, identified by NMR as 1-methylethyl 2-(4-methoxy-[1,1'-biphenyl]-3-yl)-2-ethylhydrazinecarboxylate.

Example 2

Preparation of 1-methylethyl 2-(4-methoxy-[1,1'-biphenyl]-3-yl)-2-nitrosohydrazine carboxylate (Compound #2)

To 1.5 g of the 1-methylethyl 2-(4-methoxy-[1,1'-biphenyl]-3-yl)hydrazinecarboxylate dissolved in 40 mL of methanol, was added 1 ml of concentrated hydrochloric acid and 0.6 g of sodium nitrite, to produce a reaction mixture. After stirring for 4 hours, the reaction mixture was filtered leaving 0.8 g of a yellow solid, identified by NMR as 1-methylethyl 2-(4-methoxy-[1,1'-biphenyl]-3-yl) -2-nitrosohydrazine carboxylate.

Example 3

Preparation of 1-methylethyl 2-(hydroxymethyl)-2-(4-methoxy-[1,1'-biphenyl]-3-yl) hydrazinecarboxylate (Compound #3)

To 5.3 g of 1-methylethyl 2-(4-methoxy-[1,1$^1$-biphenyl]-3-yl)hydrazinecarboxylate in 50 mL of ethanol, was added 5.3 gm of 37% formaldehyde solution. After stirring overnight, the reaction mixture was reduced in volume, diluted with 150 mL of water, and extracted with dichloromethane (2×200 mL). Work-up gave an oil which was crystallized from diethyl ether. There was obtained 1.2 gm of an off-white solid. This compound was identified by NMR as 1-methylethyl 2-(hydroxymethyl)-2-(4-methoxy-[1,1$^1$-biphenyl]-3-yl) hydrazinecarboxylate.

The remaining compounds in Table 1 were prepared using the procedure above in Example 1. Each of the compounds so formed is characterized by its NMR data.

TABLE 1

(I)

| No. | R | R' | R" | NMR Data (PPM) In CDCl$_3$ |
|---|---|---|---|---|
| 1 | C$_2$H$_5$ | CH$_3$ | CH(CH$_3$)$_2$ | m(9)1.0–1.3, q(2)3.3–3.7, s(3)3.8, m(1)4.7–5.1, m(9)6.9–7.6 |
| 2 | NO | CH$_3$ | CH(CH$_3$)$_2$ | d(6)1.2, s(3)3.8, m(9)6.9–7.6 |
| 3 | CH$_2$OH | CH$_3$ | CH(CH$_3$)$_2$ | d(6)1.2, s(3)3.8, s(2)4.7, m(1)4.7–5.1, m(9)6.9–7.6 |
| 4 | CH$_2$C$_6$H$_5$ | CH$_3$ | CH(CH$_3$)$_2$ | d(6)1.2, s(3)3.8, s(2)4.3, m(1)4.7–5.1, m(14)6.9–7.6 |
| 5 | CH$_2$CH$_2$F | CH$_3$ | CH(CH$_3$)$_2$ | d(6)1.2, m(4)3.4–4.0, s(3)3.8, m(2)4.2–5.0, m(9)6.9–7.6 |
| 6 | C$_3$H$_7$ | CH$_3$ | CH(CH$_3$)$_2$ | m(11)0.9–1.3, m(2)3.1–3.4, s(3)3.8, m(9)6.9–7.6 |

Example 4

Preparation of Formulations

The remaining examples relate to the insecticidal and miticidal use of the compounds of this invention. In all these examples, a stock solution for the compounds was prepared at 3000 ppm by dissolving 0.24 gram of each compound to be tested in 8 ml of acetone and adding 72 ml of distilled water plus 3 drops of ethoxylated sorbitan monolaurate, a wetting agent. This stock solution was used in the remaining examples demonstrating the insecticidal and miticidal use of representative compounds of this invention. For each example that follows, this stock solution was used and the specified dilutions were made. All the tests discussed below, which involved treatment with compounds of this invention, were always repeated with controls, in which the active compound was absent, to permit a comparison upon which the percent control was calculated.

Example 5

Southern Corn Rootworm Test

The stock solution of 3000 ppm was diluted to 100 ppm (test solution). For each compound, 2.5 ml of the test solution was pipetted onto a filter paper (Whatman #3) at the bottom of a 100 mm petri dish. Two corn seedlings were soaked in each test solution for 1 hour and transferred to a petri dish containing the same test solution. After 24 hours, each dish was loaded with 5 second instar larvae of Southern Corn Rootworm (*Diabrotica undecimpunctata*). After five days, the number of live larvae was noted and the percent control, corrected by Abbott's formula [see J. Economic Entomology 18: 265–267 (1925)] was calculated.

The results of this testing of southern corn rootworm (CR) are presented below in Table 2.

Example 6

Mite Adulticide and Mite Ovicide Tests

One day before treatment of cowpea primary leaves with the test solutions, a "FIG. 8" configuration of tree tanglefoot was applied to each of two cowpea primary leaves, one from each of two plants in a pot. In each figure, the circle nearer the stem was designated for the mite ovicide test and the circle further from the stem was designated for the mite adulticide test.

Groups of adult mites (*Tetranychus urticae* Koch) were transferred into each of the ovicide circles one day before treatment of the plants with the test solution. The females were allowed to deposit eggs until one hour before treatment, at which point all the adult mites were removed. The plants were then sprayed to run off with a 1000 ppm test solution diluted from the 3000 ppm stock solution.

One day following treatment of the plants with the test solution, groups of approximately 25 adult mites were transferred into each of the adulticide rings. Five days later these rings were examined for live mites remaining on the leaves. The percent control was estimated based on the number of mites surviving on the control plants.

Nine days following treatment the ovicide rings were examined for unhatched eggs and living immature mites. The percent control was estimated based on the number of unhatched eggs and living immature mites.

Results of the mite adulticide (MI) and mite ovicide (MIOV) tests are presented below in Table 2.

TABLE 2

| Compound # | Percent Control | | |
|---|---|---|---|
| | CR | MI | MIOV |
| 1 | 60 | 100 | 100 |
| 2 | 0 | 100 | 100 |
| 3 | 0 | 100 | 70 |
| 4 | 40 | 100 | 100 |
| 5 | 0 | 100 | 0 |
| 6 | 50 | 95 | 0 |

What is claimed is:

1. A compound of the formula

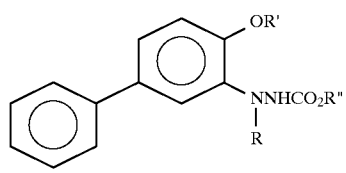

wherein:

R is $C_2$–$C_6$ alkyl or $C_7$–$C_9$ aralkyl;

R' is $C_1$–$C_4$ alkyl; and

R" is $C_1$–$C_4$ alkyl.

2. A compound as recited in claim 1 wherein R is $C_2$–$C_4$ alkyl or $C_7$–$C_9$ aralkyl.

3. A compound as recited in claim 2 wherein R' is methyl and R" is isopropyl.

4. A compound as recited in claim 3 wherein R is ethyl, propyl or benzyl.

5. An insecticidal composition comprising:
  a) an effective amount of a compound as recited in claim 1; and
  b) a suitable carrier.

6. An insecticidal composition comprising:
  a) an effective amount of a compound as recited in claim 2; and
  b) a suitable carrier.

7. An insecticidal composition comprising:
  a) an effective amount of a compound as recited in claim 3; and
  b) a suitable carrier.

8. An insecticidal composition comprising:
  a) an effective amount of a compound as recited in claim 4; and
  b) a suitable carrier.

9. A miticidal composition comprising:
  a) an effective amount of a compound as recited in claim 3; and
  b) a suitable carrier.

10. A miticidal composition comprising:
  a) an effective amount of a compound as recited in claim 3; and
  b) a suitable carrier.

11. A miticidal composition comprising:
  a) an effective amount of a compound as recited in claim 3; and
  b) a suitable carrier.

12. A miticidal composition comprising:
  a) an effective amount of a compound as recited in claim 4; and
  b) a suitable carrier.

13. A method for controlling insects which comprises applying to a locus to be protected an effective amount of a compound as recited in claim 1.

14. A method for controlling insects which comprises applying to a locus to be protected an effective amount of a compound as recited in claim 2.

15. A method for controlling insects which comprises applying to a locus to be protected an effective amount of a compound as recited in claim 3.

16. A method for controlling insects which comprises applying to a locus to be protected an effective amount of a compound as recited in claim 4.

17. A method for controlling mites which comprises applying to a locus to be protected an effective amount of a compound as recited in claim 1.

18. A method for controlling mites which comprises applying to a locus to be protected an effective amount of a compound as recited in claim 2.

19. A method for controlling mites which comprises applying to a locus to be protected an effective amount of a compound as recited in claim 3.

20. A method for controlling mites which comprises applying to a locus to be protected an effective amount of a compound as recited in claim 4.

* * * * *